United States Patent [19]

Dyrud et al.

[11] Patent Number: 5,195,539

[45] Date of Patent: Mar. 23, 1993

[54] EARPLUG COMPRESSION DEVICE

[75] Inventors: James F. Dyrud, New Richmond, Wis.; Gerald V. Elstran, Stillwater, Minn.

[73] Assignee: Minnesota Mining and Manufacturing Company, St. Paul, Minn.

[21] Appl. No.: 855,316

[22] Filed: Mar. 23, 1992

[51] Int. Cl.$^5$ .............................................. A61F 11/00
[52] U.S. Cl. .................................... 128/864; 128/865
[58] Field of Search ........................... 128/864–868, 128/878, 876, 877, 885; 602/15, 20, 21, 52

[56] References Cited

U.S. PATENT DOCUMENTS

| | | | |
|---|---|---|---|
| Re. 29,487 | 12/1977 | Gardner, Jr. | 128/152 |
| 2,998,008 | 8/1961 | Klesa | 128/878 |
| 3,256,880 | 6/1966 | Caypinar | 128/877 |
| 3,423,095 | 1/1969 | Cox | 128/877 |
| 3,521,625 | 7/1970 | Mackey | 128/877 |
| 4,158,087 | 6/1979 | Wood | 521/137 |
| 4,160,449 | 7/1979 | Wade | 128/152 |
| 4,198,989 | 4/1980 | Hawke | 128/877 |
| 4,219,018 | 8/1980 | Draper Jr. | 128/152 |
| 4,254,766 | 3/1981 | Kordis | 128/877 |
| 4,503,849 | 3/1985 | Morgan | 128/877 |
| 4,579,112 | 4/1986 | Scott | 128/151 |
| 4,729,138 | 3/1988 | Heyman | 128/878 |
| 4,774,938 | 10/1988 | Leight | 128/864 |
| 4,910,831 | 3/1990 | Bingold | 128/878 |
| 5,044,463 | 9/1991 | Carr | 181/135 |
| 5,074,292 | 12/1991 | Cox | 128/878 |
| 5,076,289 | 12/1991 | Darling | 128/877 |
| 5,321,998 | 3/1982 | Van de Walker et al. | 206/229 |

OTHER PUBLICATIONS

Booklet No. 1-589-5M-HP, Cabot Corp. (1988) "How To Make Sure You Get The Best From Your E-A-R Plugs".

Primary Examiner—Robert A. Hafer
Assistant Examiner—Michael Brown
Attorney, Agent, or Firm—Gary L. Griswold; Walter N. Kirn; Carole Truesdale

[57] ABSTRACT

A device for compressing slow recovery earplugs is provided. The device comprises a flexible strip having an elongate compression portion having first and second ends and a base portion at the first end of the compression portion, the base portion having a width greater than that of the compression portion, an opening proximate the compression portion and having a width transverse of the compression portion larger than the width of the compression portion, the compression portion being at least 15 mm wide and of sufficient length that the second end can pass through the opening to form a tubular compression means having a diameter at least that of a slow recovery earplug.

11 Claims, 1 Drawing Sheet

EARPLUG COMPRESSION DEVICE

BACKGROUND OF THE INVENTION

1. Field of the Invention

The invention relates to an earplug compression device which aids in insertion of a slow-recovery earplug into the human ear canal.

2. Description of the Related Art

U.S. Pat. No. RE. 29,487 (Gardner, Jr.) describes earplugs of generally cylindrical shape and of somewhat larger diameter than the human ear canal. The earplugs are composed of a foamed plasticized polymeric material having a sufficiently high concentration of plasticizer to provide the earplug with a reduced rate of recovery from compression. The earplugs can be compressed by twirling lengthwise between the fingers. The compressed earplug is inserted into the ear canal where it then recovers slowly until it conforms to and obturates the ear canal, thus suppressing or attenuating the transmission of noise.

Booklet No. 1-589-5M-HP (1988), "How To Make Sure You Get The Best Fit From Your E-A-R Plugs", available from Cabot Corp. describes a device for training people to use slow-recovery earplugs of the type described in the Gardner patent. The device includes a Roll Model TM transparent block having cylindrical holes of graduated size. An uncompressed earplug is rolled between the fingertips until tightly compressed to form a very thin crease-free cylinder. The adequacy of compression is then evaluated by determining into which, if any, of the holes in the Roll Model TM block the compressed earplug will fit. When proper compression techniques have been learned, the compressed earplug can be inserted in the ear to a depth of about ½ the length of the ear canal. The booklet indicates that acquiring such skills is necessary because insertion into the ear canal to lesser depths causes wearers' perception of their own voices and body noises to be distorted, wearers with larger ear canals may push an earplug in so forcefully and quickly that it becomes difficult to grasp and remove as well as uncomfortable. To guard against this, the earplug can be rolled into the shape of a golf tee.

U.S. Pat. No. 4,774,938 (Leight) discloses a slow recovery earplug which has open cells for expelling gas to the outside during compression, but which resists the entry of water through the outside and the soiling of the outside by dirt. The earplug includes a body formed of pressure-molded slow recovery resilient foam material forming multiple gas-filled shells. The plug body has a surface region forming a skin which is primarily continuous and has a flanged or flared rear end that limits the depth of insertion of the earplug into the ear and provides a region to be grasped to remove the earplug.

U.S. Pat. No. 4,160,449 (Wade) discloses an earplug comprising a generally cylindrical plug of soft compressible resilient spongy material, such as elastomeric foam, having a diameter in relaxed condition slightly larger than the canal of a human ear. The plug is encased in an envelope of thin flexible plastic material which extends lengthwise beyond the end of the plug. The envelope is twistable to compress the plug and thereby reduce its size so as to facilitate introduction of the plug into the human ear canal. The envelop can be open to the atmosphere to permit air to be expelled when the envelop is compressed and twisted, or the envelop can be sealed and evacuated.

U.S. Pat. No. 5,044,463 (Carr) discloses a bullet-shaped molded foam earplug which is provided with a cavity extending from the flanged base axially into the earplug. The cavity provides an earplug which exerts less pressure on the ear canal than an earplug containing no cavity, thus, making the earplug more comfortable.

U.S. Pat. No. 4,579,112 (Scott) discloses an earplug which does not enter the ear canal but which merely blocks the entrance of the canal. The plug is made of a closed cell elastomeric foam having a tear drop ellipsoid shape when viewed from the side. The plug is slightly compressed and placed in a clocking position behind the tragus.

U.S. Pat. No. 4,219,018 (Draper, Jr.) disclosed an earplug unit with an inserter and tie adapted to be worm as a unit comprising one or a pair of earplugs each having a relatively flexible stem portion and adjacent spaced flanges of varying size made of relatively soft, yieldable, resilient material which readily conforms to sealingly engage the wall of the auditory canal of an ear. Each earplug has outer end attached to one or both ends of a tie member on which is slideably carried and retained an earplug inserter movable from a carrying position into engagement with the outer end of an earplug for its insertion into the auditory canal of an ear.

U.S. Pat. No. 4,321,998 (Van de Walker et al.) discloses a combined protective case and inserter for earplugs which has a cover held in a closed or an open position by a frictional backing feature, and can be reversed whereby either one of two earplug inserting means are exposed externally for the case for aiding the insertion of the earplug into a users ear. The earplugs useful with the invention are flange-type earplugs similar to those described in Draper, Jr.

SUMMARY OF THE INVENTION

The present invention provides a device for compressing slow recovery earplugs comprising a flexible strip having an elongate compression portion having first and second ends and a base portion at the first end of the compression portion, the base portion having a width greater than that of the compression portion, an opening proximate the compression portion and having a width transverse of the compression portion larger than the width of the compression portion, the compression portion being at least 15 mm wide and of sufficient length that the second end can pass through the opening to form a tubular compression means having a diameter at least that of a slow recovery earplug and so that when a slow recovery earplug is positioned in the tubular compression means and tension is applied between the second end and the base portion, the part of the compression portion between the base portion and the opening will decrease to radially compress the slow recovery earplug.

The device of the present invention provides a means for ensuring that the slow-recovery earplug is properly compressed prior to insertion in the ear canal and remains clean during compression.

The present invention further provides a method for providing a compressed slow recovery earplug comprising a flexible strip having an elongate compression portion having first and second ends and a base portion at the first end of the compression portion, the base portion having a width greater than that of the compression portion, an opening proximate the compression portion and having a width transverse of the compression portion larger than the width of the compression portion, the compression portion being at least 15 mm wide, inserting the second end of the compression portion through the opening to form an annular space, positioning a slow recovery earplug in the annular space, and pulling the second end of the compression portion to compress the earplug.

DETAILED DESCRIPTION OF THE INVENTION

Figure 3:
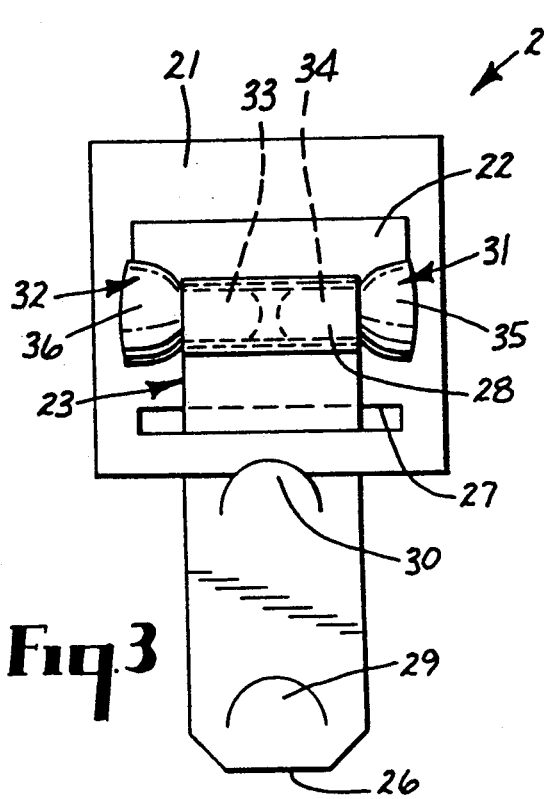
FIG. 3 is a top view of the device of the invention with the compression portion radially compressing earplugs.

The device of the invention can be formed of any material which is flexible enough to form a convoluted roll having a diameter of about 5 mm and a tensile strength sufficient to provide compression of the earplugs without tearing. Such materials include, for example, papers, foils, fabrics and plastic films. Plastic film is generally preferred. Plastic films and foils useful in the present invention are preferably about 0.1 to 0.5 mm, more preferably 0.25 mm, in thickness. Paper useful in the present invention is preferably from 0.2 to 1 mm, more preferably about 0.5 mm, in thickness. Biodegradable papers may be preferred because of environmental concerns.

When in use the inside diameter of the compression portion should be sufficiently less than the diameter of the human ear canal to compress the earplug to less than the diameter of the ear canal. The average adult ear canal has a diameter of about 9 mm although some adult ear canals may have diameters as small as about 6.5 mm. Therefore, the compression portion preferably is capable of having an inside diameter of less than about 8 mm, more preferably less than about 6 mm, most preferably less than about 5 mm.

The compression portion is of sufficient length to permit the portion to wrap around an earplug and protrude through the opening in the base portion. Generally, a length of about 40 mm is sufficient. In a preferred embodiment of the invention, the compression portion is of a sufficient length that two convolutions can be wrapped around the earplug. This tends to provide mechanical advantage and more uniform compression of the earplugs.

Generally, the width of the compression portion of the device of the invention should be at least as wide as that portion of the earplug which is to be compressed. The compressed portion of the earplug should be elongated and of sufficient length to extend beyond the ossio-tympanic junction of the ear canal without contacting the eardrum. The compressed portion is preferably about 15 to 25 mm, more preferably about 17 mm, in length. Thus, the compression portion is at least about 15 mm, preferably at least about 17 mm, in width. More preferably, the device is of sufficient width that a pair of earplugs can be compressed simultaneously.

Preferably, a short length of the earplug protrudes beyond the end of the compression portion and forms a bulbous portion which has a diameter greater than that of the human ear canal. The bulbous portion is useful for removing the earplug from the compression means, inserting the earplug into the ear canal, and removing the earplug from the ear canal after use. The bulbous end can prevent insertion of the earplug too far into the ear canal and can serve as an indication that the desired length of the earplug has been inserted. The bulbous end preferably comprises from 20 to 40% of the total length of the earplug.

The base portion is of a size sufficient to provide the opening through which the compression portion slides and convenient for grasping the device. Preferably, the base portion is at least about 1 to 2 cm wider than the compression portion. The base portion may be of the same or a different material as the compression portion. The base portion and the compression portion may be a unitary strip.

In a preferred embodiment of the invention, the base portion is attached to a platform which is relatively stiff to aid in grasping and using the device of the invention. Such a platform can also be for paper, foil or plastic and attachment can be made by any well-known means such as by adhesive or stapling.

The slow-recovery earplugs useful with the device of the present invention are generally formed from polymeric foam materials and are well known to those skilled in the art. The earplug must be sufficiently compressible that it can be compressed by the compression means and sufficiently resilient that it will expand to fit an ear canal. Such earplug materials are disclosed, for example, in U.S. Pat. No. RE. 29,487 (Gardner, Jr.), U.S. Pat. No. 4,774,938 (Leight) and U.S. Pat. No. 4,158,087 (Wood), each of which is incorporated by reference herein.

To ensure that the earplug remains snugly in place after being inserted into an ear canal, the diameter to which it fully recovers after removal from the compression means should be slightly larger than the diameter of the human ear canal. To make earplugs of significantly larger diameter would be wasteful of material and would make them less comfortable to wear. For the great majority of wearers, that portion of the earplug that is compressed preferably recovers freely to an average diameter of at least about 10 mm, more preferably at least about 12 mm, most preferably at least about 15 mm. When the inserted earplug extends beyond the ossio-tympanic junction of the ear canal and is left in place for an appreciable length of time, that portion which contacted the ossio-tympanic junction exhibits a tiny depression immediately after removal from the ear canal.

In a preferred embodiment of the invention, uncompressed earplugs are provided with the device and the compression portion is provided inserted in the opening. A locking means, such as a locking tab or releasable adhesive, is preferably provided to hold the compression portion at the proper tension. Optionally, additional locking means can be provided on the compression portion to indicate proper compression of the earplugs.

The present invention is further described as follows with reference to the drawing.

Figure 1:
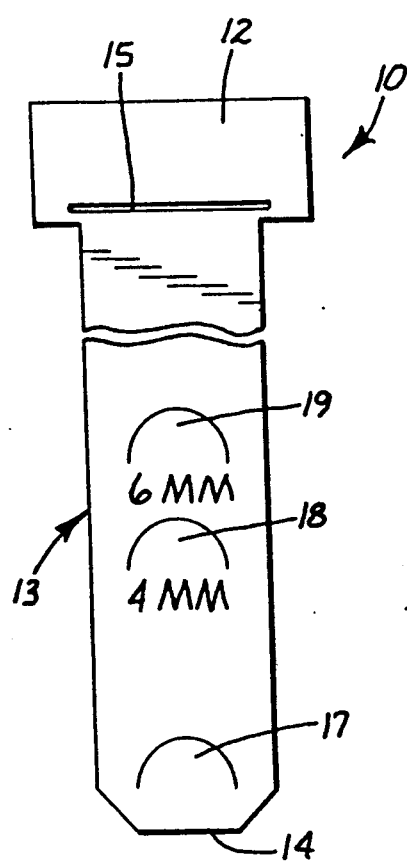
FIG. 1 is a top view of the device of the invention.

In FIG. 1, a device 10 of the invention includes a base portion 12 and a compression portion 13, the first end of the compression portion being attached to the base portion. The base portion 12 is provided with opening 15 through which the second end 14 of compression portion 13 may be inserted. Optional locking tabs 17, 18 and 19 are provided in compression portion 13.

Figure 2:
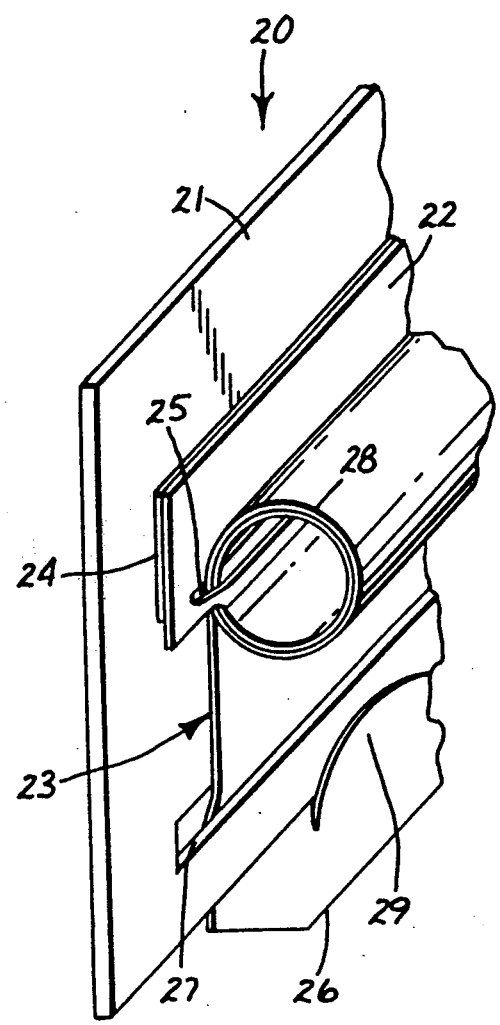
FIG. 2 is a partial perspective view of the device of the invention.

In FIG. 2, a preferred embodiment of the device of the invention is shown ready for use. The device 20 includes base portion 22 mounted on platform 21 by adhesive 24. Opening 25 is provided in base portion 22. Compression portion 23 has been wrapped to form tubular compression means strip 28. The second end 26 of compression portion 23 has been inserted through opening 27 in platform 21 and is held in place by locking tab 29. The device can be used by inserting earplugs in the device and pulling on second end 26 of compression portion 23.

In FIG. 3, the device of FIG. 2 is shown in use. Earplugs 31 and 32 have been inserted in tubular compression means 28 of compression portion 23. Second end 26 of compression portion 23 has been pulled to decrease the diameter of tubular compression means strip 28 and compress portions 33, 34 of earplugs 31, 32. A portion of each earplug is left uncompressed to form bulbous ends 35, 36. The desired degree of compression is achieved by pulling second end 26 sufficiently to engage indicator locking tab 30.

The following non-limiting example serves to illustrate the device.

EXAMPLE

A device like that shown in FIGS. 2 and 3 was made using a strip of polyester plastic film having a thickness of 0.12 mm, a width 48 mm at the base portion and 38 mm at the compression portion. The total length was 130 mm with the compression portion extending 120 mm beyond the opening in the base portion. The base portion was attached to a cardboard platform 6 cm × 6 cm in size. An opening 0.5 mm long and 39 mm wide was provided in the base portion. The compression portion was inserted through the opening to form a tubular compression means having two convolutions. Slow recovery earplugs having a tapered bullet shape and a substantially spherical tip with a diameter of 11 mm at the tip, a diameter of 15 mm at the blunt end and a length of 24 mm were inserted in each end of the tubular compression means such that about 7 mm of the earplug protruded from the tubular compression means. The end of the compression portion was inserted through a slot in the cardboard platform until a locking tab was engaged to compress the earplugs to a diameter about one mm less than when uncompressed. The earplugs are thus retained in the device until use.

The free end of the compression portion was pulled to compress portions of the earplugs within the tubular compression means to a diameter of 4 mm. The tension was released from the compression portion to permit easy removal of the compressed earplugs. Each earplug was readily inserted into a human ear canal. The compressed portions of the earplugs gradually expanded to become snugly fitted into the ear canals.

What is claimed is:

1. A device for compressing slow recovery earplugs comprising a flexible strip having an elongate compression portion having first and second ends and a base portion at said first end of said compression portion, said base portion having a width greater than that of said compression portion, an opening proximate said compression portion and having a width transverse of said compression portion larger than the width of said compression portion, said compression portion being at least 15 mm wide and of sufficient length that said second end can pass through said opening to form a tubular compression means having a diameter at least that of a slow recovery earplug and so that when a slow recovery earplug is positioned in said tubular compression means and tension is applied between said second end and said base portion, the part of said compression portion between said base portion and said opening will decrease to radially compress said slow recovery earplug.

2. The device of claim 1 wherein said flexible strip is paper, foil or plastic film.

3. The device of claim 1 wherein said flexible strip is plastic film having a thickness of about 0.1 to 0.5 mm.

4. The device of claim 1 further comprising a platform adhered to said base portion.

5. The device of claim 4 wherein said compression portion is provided with locking means for locking engagement with said platform.

6. The device of claim 5 wherein said platform has a first side parallel and extending beyond said base portion opening and is provided with an opening proximate and parallel said first side and said compression portion is provided with arcuate slits adapted for locking engagement with said first side when said compression means has been inserted through said opening of said platform.

7. The device of claim 1 wherein said compression portion is at least about 40 mm long.

8. A device for compressing slow recovery earplugs comprising a flexible strip having an elongate compression portion having first and second ends and a base portion at said first end of said compression portion, said base portion having a width greater than that of said compression portion, an opening proximate said compression portion and having a width transverse of said compression portion larger than the width of said compression portion, said compression portion being at least 15 mm wide and inserted through said opening to form an annular space and a slow recovery earplug inserted in said annular space so that when tension is applied between said second end and said base portion the part of said compression portion between said base portion and said opening will decrease to radially compress said slow recovery earplug.

9. A device for compressing slow recovery earplugs comprising a platform and a flexible strip having an elongate compression portion having first and second ends and a base portion at said first end of said compression portion, said base portion being attached to said platform and having a width greater than that of said compression portion, an opening proximate said compression portion and having a width transverse of said compression portion larger than the width of said compression portion, said compression portion being at least 15 mm wide and inserted through said opening to form an annular space and a slow recovery earplug inserted in said annular space so that when tension is applied between said second end and said base portion the part of said compression portion between said base portion and said opening will decrease to radially compress said slow recovery earplug.

10. A method for providing a compressed slow recovery earplug comprising providing a flexible strip having an elongate compression portion having first and second ends and a base portion at said first end of said compression portion, said base portion having a width greater than that of said compression portion, an opening proximate said compression portion and having a width transverse of said compression portion larger than the width of said compression portion, said compression portion being at least 15 mm wide, inserting said second end of said compression portion through said opening to form an annular space, positioning a slow recovery earplug in said annular space, and pulling said second end of said compression portion to compress said earplug.

11. A device for compressing slow recovery earplugs comprising a flexible strip formed from paper, foil or plastic, having an elongate compression portion having first and second ends and a base portion at said first end of said compression portion, said base portion having a width greater than that of said compression portion, an opening proximate said compression portion and having a width transverse of said compression portion larger than the width of said compression portion, said compression portion being at least 15 mm wide and of sufficient length that said second end can pass through said opening to form a tubular compression means having a diameter at least that of a slow recovery earplug and so that when a slow recovery earplug is positioned in said tubular compression means and tension is applied between said second and said base portion, the part of said compression portion between said base portion and said opening will decrease to radially compress said slow recovery earplug.

* * * * *